(12) United States Patent
Sannholm et al.

(10) Patent No.: US 10,368,799 B2
(45) Date of Patent: Aug. 6, 2019

(54) SYSTEM FOR DETERMINING THE QUALITY OF SLEEP

(71) Applicant: Apple Inc., Cupertino, CA (US)

(72) Inventors: Fredrik Sannholm, Espoo (FI); Joonas Paalasmaa, Helsinki (FI); Lasse Leppakorpi, Kirkkonummi (FI)

(73) Assignee: APPLE INC., Cupertino, CA (US)

( * ) Notice: Subject to any disclaimer, the term of this patent is extended or adjusted under 35 U.S.C. 154(b) by 0 days.

(21) Appl. No.: 14/997,031

(22) Filed: Jan. 15, 2016

(65) Prior Publication Data

US 2016/0213309 A1 Jul. 28, 2016

Related U.S. Application Data

(60) Provisional application No. 62/108,149, filed on Jan. 27, 2015.

(51) Int. Cl.
*A61B 5/00* (2006.01)
*A61B 5/11* (2006.01)
*A61B 5/08* (2006.01)
*A61B 5/113* (2006.01)
*G06F 19/00* (2018.01)

(52) U.S. Cl.
CPC ........... *A61B 5/4815* (2013.01); *A61B 5/08* (2013.01); *A61B 5/1116* (2013.01); *A61B 5/7271* (2013.01); *A61B 5/1102* (2013.01); *A61B 5/113* (2013.01); *A61B 5/6892* (2013.01); *A61B 5/7264* (2013.01); *A61B 5/7282* (2013.01); *A61B 2562/0257* (2013.01); *A61B 2562/0261* (2013.01); *G06F 19/30* (2013.01)

(58) Field of Classification Search
CPC ............................... A61B 5/4815; A61B 5/08
USPC ................................................. 600/300–301
See application file for complete search history.

(56) References Cited

U.S. PATENT DOCUMENTS

| 5,479,939 A | 1/1996 | Ogino |
| 5,483,261 A | 1/1996 | Yasutake |
| 5,488,204 A | 1/1996 | Mead et al. |

(Continued)

FOREIGN PATENT DOCUMENTS

| EP | 2278507 | 1/2011 |
| EP | 2301429 | 3/2011 |

(Continued)

OTHER PUBLICATIONS

International Search Report and Written Opinion of the International Searching Authority PCT/FI2015/050959 dated Apr. 8, 2016.

(Continued)

*Primary Examiner* — Carl H Layno
*Assistant Examiner* — Dacheng Xie
(74) *Attorney, Agent, or Firm* — Morrison & Foerster LLP (57) ABSTRACT

Embodiments of the present invention provide a distributed computer system and a method for determining the quality of sleep of a sleeping user. The distributed computer system will determine the quality of sleep by detecting the changes in body posture of the sleeping user. The quality of sleep will be determined by the feature vectors associated with each posture of the sleeping user. The posture of the user will be determined by recording a body motion signal caused by the mechanical and muscle movement of the body of the user.

18 Claims, 8 Drawing Sheets

(56) References Cited

U.S. PATENT DOCUMENTS

| | | | |
|---|---|---|---|
| 5,825,352 | A | 10/1998 | Bisset et al. |
| 5,835,079 | A | 11/1998 | Shieh |
| 5,880,411 | A | 3/1999 | Gillespie et al. |
| 6,188,391 | B1 | 2/2001 | Seely et al. |
| 6,310,610 | B1 | 10/2001 | Beaton et al. |
| 6,323,846 | B1 | 11/2001 | Westerman et al. |
| 6,425,861 | B1 | 7/2002 | Haberland |
| 6,690,387 | B2 | 2/2004 | Zimmerman et al. |
| 7,015,894 | B2 | 3/2006 | Morohoshi |
| 7,164,941 | B2 | 1/2007 | Misczynski et al. |
| 7,166,952 | B2 | 1/2007 | Topliss et al. |
| 7,184,064 | B2 | 2/2007 | Zimmerman et al. |
| 7,442,107 | B1 | 10/2008 | Ueda et al. |
| 7,663,607 | B2 | 2/2010 | Hotelling et al. |
| 8,003,982 | B2 | 8/2011 | Wang et al. |
| 8,161,826 | B1 | 4/2012 | Taylor |
| 8,479,122 | B2 | 7/2013 | Hotelling et al. |
| 2004/0225179 | A1 | 11/2004 | Kaplan et al. |
| 2005/0042589 | A1 | 2/2005 | Hallestad et al. |
| 2005/0124864 | A1 | 6/2005 | Mack et al. |
| 2005/0190068 | A1 | 9/2005 | Gentry et al. |
| 2005/0209513 | A1 | 9/2005 | Heruth et al. |
| 2005/0234314 | A1 | 10/2005 | Suzuki et al. |
| 2005/0257822 | A1 | 11/2005 | Smith et al. |
| 2006/0169282 | A1 | 8/2006 | Izumi et al. |
| 2006/0197753 | A1 | 9/2006 | Hotelling |
| 2007/0118054 | A1* | 5/2007 | Pinhas ................. A61B 5/1101 600/587 |
| 2007/0156060 | A1 | 7/2007 | Cervantes |
| 2008/0306351 | A1* | 12/2008 | Izumi ..................... A61B 5/113 600/300 |
| 2010/0016685 | A1 | 1/2010 | Muehlsteff et al. |
| 2010/0201650 | A1 | 8/2010 | Son |
| 2010/0240982 | A1 | 9/2010 | Westbrook et al. |
| 2010/0331632 | A1 | 12/2010 | Chou |
| 2011/0010014 | A1 | 1/2011 | Oexman et al. |
| 2011/0015467 | A1 | 1/2011 | Dothie |
| 2011/0190594 | A1 | 8/2011 | Heit et al. |
| 2011/0224510 | A1* | 9/2011 | Oakhill .................... A61B 5/11 600/301 |
| 2011/0230790 | A1 | 9/2011 | Kozlov |
| 2012/0004523 | A1 | 1/2012 | Richter et al. |
| 2012/0092171 | A1 | 4/2012 | Hwang et al. |
| 2012/0215076 | A1 | 8/2012 | Yang et al. |
| 2013/0015866 | A1 | 1/2013 | Wendt et al. |
| 2013/0030257 | A1 | 1/2013 | Nakata et al. |
| 2013/0060097 | A1 | 3/2013 | Rubin |
| 2013/0066168 | A1 | 3/2013 | Yang et al. |
| 2013/0178715 | A1 | 7/2013 | Sakai et al. |
| 2013/0245502 | A1* | 9/2013 | Lange ................. A61B 5/1101 600/595 |
| 2013/0261404 | A1 | 10/2013 | Sato |
| 2013/0326811 | A1 | 12/2013 | Miles |
| 2014/0005502 | A1 | 1/2014 | Klap |
| 2014/0046184 | A1* | 2/2014 | Heinrich ............... A61B 5/0064 600/438 |
| 2014/0247146 | A1 | 9/2014 | Proud |
| 2014/0269224 | A1 | 9/2014 | Huh et al. |
| 2014/0276245 | A1 | 9/2014 | Tsutsumi |
| 2014/0288385 | A1 | 9/2014 | Amurthur et al. |
| 2014/0337450 | A1 | 11/2014 | Choudhary |
| 2015/0011899 | A1 | 1/2015 | Shigeto et al. |
| 2015/0367097 | A1 | 12/2015 | Gavish |
| 2016/0022218 | A1* | 1/2016 | Hayes ................... A61G 7/005 600/301 |
| 2016/0106339 | A1* | 4/2016 | Behzadi ............... A61B 5/0022 600/302 |
| 2016/0252411 | A1 | 9/2016 | Benaissa et al. |
| 2018/0028111 | A1 | 2/2018 | Waris |
| 2018/0042556 | A1 | 2/2018 | Shahparnia |
| 2018/0337325 | A1 | 11/2018 | Han |

FOREIGN PATENT DOCUMENTS

| | | |
|---|---|---|
| EP | 2 644 087 A1 | 10/2013 |
| EP | 2 783 725 A1 | 10/2014 |
| JP | 63-016237 A | 1/1988 |
| JP | 2000-163031 A | 6/2000 |
| JP | 2002-342033 A | 11/2002 |
| JP | 2004-113618 A | 4/2004 |
| JP | 2008-183181 A | 8/2008 |
| JP | 2009-233027 A | 10/2009 |
| JP | 2012-170471 A | 9/2012 |
| WO | WO-2006/131855 A2 | 12/2006 |
| WO | WO-2006/131855 A3 | 12/2006 |
| WO | WO-2012/122002 A1 | 9/2012 |
| WO | 2013-179189 | 12/2013 |
| WO | WO-2015/008285 A1 | 1/2015 |
| WO | WO-2015/075692 A1 | 5/2015 |
| WO | WO-2016/087709 A1 | 6/2016 |
| WO | WO-2016/124817 A1 | 8/2016 |
| WO | WO_2018_217585 A1 | 11/2018 |

OTHER PUBLICATIONS

Lei Song et al., "Health Sensing by Wearable Sensors and Mobile Phones: A Survey", Conference Proceedings Article of the 16th International Conference on e-Health Networking, Applications and Services (Healthcom), p. 453-459, Oct. 15, 2014.

Joonas Paalasmaa et al., "Unobtrusive Online Monitoring of Sleep at Home", Conference Proceeding Article, 34th Annual International Conference of the IEEE EMBS, p. 3784-3788, Aug. 28, 2012.

Bischoff, "Quantified sleep: a new gadget from China wants to get in bed with you," accessed at https://www.techinasia.com/quantified-sleep-gadget-china-bed/, accessed on Nov. 27, 2014, pp. 1-6.

Kortelainen et al., "PCA model for recording respiration and posture with multichannel BCG sensor in bed mattress," presented at the 4th pHealth Conf., Porto Carras, Greece, Jun. 20-22, 2007, pp. 1-5.

Final Office Action dated Aug. 22, 2016, for U.S. Appl. No. 14/934,472, filed Nov. 6, 2015, 14 pages.

International Search Report, dated Feb. 5, 2016, for PCT Application No. PCT/FI2015/050751, twelve pages.

International Search Report dated Apr. 25, 2016, for PCT Application No. PCT/FI2016/050048, filed Jan. 28, 2016, ten pages.

Kortelainen et al. (May 2010). "Sleep Staging Based on Signals Acquired Through Bed Sensor," IEEE Transactions on Information Technology in Biomedicine,vol. 14, No. 3, pp. 776-785.

Non-Final Office Action dated Mar. 11, 2016, for U.S. Appl. No. 14/934,472, filed Nov. 6, 2015, ten pages.

Non-Final Office Action dated Jan. 3, 2017, for U.S. Appl. No. 14/934,472, filed Nov. 6, 2015, twelve pages.

Paalasmaa, J. (2014). "Monitoring Sleep with Force Sensor Measurement," University of Helsinki, Department of Computer Science, Series of Publication A, Report A-2014-2, 69 pages.

Lee, S.K. et al. (Apr. 1985). "A Multi-Touch Three Dimensional Touch-Sensitive Tablet," *Proceedings of CHI: ACM Conference on Human Factors in Computing Systems*, pp. 21-25.

Rubine, D.H. (Dec. 1991). "The Automatic Recognition of Gestures," CMU-CS-91-202, Submitted in Partial Fulfillment of the Requirements for the Degree of Doctor of Philosophy in Computer Science at Carnegie Mellon University, 285 pages.

Rubine, D.H. (May 1992). "Combining Gestures and Direct Manipulation," CHI '92, pp. 659-660.

Westerman, W. (Spring 1999). "Hand Tracking, Finger Identification, and Chordic Manipulation on a Multi-Touch Surface," a Dissertation Submitted to the Faculty of the University of Delaware in Partial Fulfillment of the Requirements for the Degree of Doctor of Philosophy in Electrical Engineering, 364 pages.

International Search Report dated Feb. 6, 2018, for PCT Application No. PCT/US2017/046521, filed Aug. 11, 2017, eight pages.

Final Office Action dated Sep. 22, 2017, for U.S. Appl. No. 14/934,472, filed Nov. 6, 2015, 12 pages.

Non-Final Office Action dated Mar. 8, 2019, for U.S. Appl. No. 15/548,744, filed Aug. 3, 2017, 15 pages.

(56) References Cited

OTHER PUBLICATIONS

Final Office Action dated Apr. 5, 2019, for U.S. Appl. No. 14/934,472, filed Nov. 6, 2015, 12 pages.
Dagdeviren, C. et al. (Dec. 1, 2016). "Recent Progress in Flexible and Stretchable Piezoelectric Devices for Mechanical Energy Harvesting, Sensing and Actuation", *Extreme Mechanics Letters*, vol. 9: 269-281.
Feng, X. et al. Mar. 23, 2011 "Stretchable Ferroelectric Nanoribbons with Wavy Configurations on Elastomeric Substrates", *ACS NANO*, 5(4):3326-3332 (p. 3329, col. 1, paragraph 2— col. 2, paragraph 1 figure 3.).
International Search Report dated Jul. 30, 2018, for PCT Application No. PCT/US2018/033534, filed May 18, 2018, five pages.
Non-Final Office Action dated Sep. 27, 2018, for U.S. Appl. No. 14/934,472, filed Nov. 6, 2015, 11 pages.

\* cited by examiner

SYSTEM FOR DETERMINING THE QUALITY OF SLEEP

FIELD OF INVENTION

The present invention relates to a system for determining the quality of sleep of a sleeping user. More particularly, the present invention is related to a system and a method for determining the quality of sleep by detecting the changes in body posture of the sleeping user.

BACKGROUND OF INVENTION

Sleeping habits have been considered an important factor for the physical and physiological wellbeing of human beings. Bad sleeping habits may lead to many health disorders. Hence, there is a need for monitoring sleep to analyze fitness of human beings.

For example, there is a technique known as ballistocardiography to determine repetitive movements of a human body. Ballistocardiography has been used in art for clinical purposes like monitoring human health, respiration rate and heartbeat etc. Ballistocardiographic measurements comprise measurement of force generated due to the cardiac function of the body, movement due to respiration and other muscle movements of the human being.

There are quite a few systems known in the prior art based on this technique, for example, a US patent application 2010/0016685 discloses a system for detecting body movements using a ballistocardiographic sensor and a noise sensor. However, this patent application does not disclose any means for detecting posture change, or what the posture of a sleeping user is at a given time. This document is incorporated here as reference.

There are also prior art devices known to allege that they detect posture of user while sleeping, for example, there is a RestOn device and application for monitoring sleep of a user, particularly to determine how many times a user has changed posture while sleeping. The RestOn device uses a strip of sensors for this purpose; however, it is not very efficient for determining the exact body posture of the user. This App is publicly available in the Apple iOS App Store. The Techinasia news article is cited here as reference, please see references section.

There are other more complex systems and methods also known in the prior art for monitoring sleep using video recorders and/or radars. For example, US patent application 2007/0156060 discloses a system for automatically monitoring the sleep of a person using a video recorder for recording live images of a subject sleeping. However, such systems are complex and expensive, and not effective during night and/or in dark rooms. Further, realization of such devices as a consumer application is not easy and they may even create hindrance in a user's sleep. This document is also incorporated here as reference.

As seen, none of the available prior art disclosures provide any method of determining the quality of sleep by analyzing the body posture and accurately distinguishing static body posture changes from minor body movements.

In light of the above discussion, there is a need for a system that can overcome one or more problems associated with the prior art.

SUMMARY OF INVENTION

The invention under study is directed towards a system and a method for effectively determining the quality of sleep of at least one user. The present invention discloses a method of determining a quality of sleep of the at least one user using a peripheral device. As said, ballistocardiographic measurements comprise measurement of force generated due to the cardiac function of the body, movement due to respiration and other muscle movements of the human being. In this invention a somewhat similar "body motion signal" is used, but this signal does not necessarily comprise a cardiogram. The body motion signal of the invention is a signal that comprises the signal generated by the skeletal muscles and at least one internal organ, such as the lungs and/or the heart. "Body motion signal" is construed as explained in the preceding sentence throughout this application. The peripheral device includes at least one sensor that records a body motion signal occurring due to mechanical and muscle movements of the body of the at least one user.

The method initiates by arranging a communication connection between the peripheral device and a mobile subscriber terminal. Further, the peripheral device communicates the body motion signal to a third party software application. The mobile subscriber terminal includes a processor for executing the third party software application. The quality of sleep is determined from the body motion signal based on the detected body posture changes.

It is a further object of the present invention to provide a method of communicating the quality of sleep by determining the body movements and posture change of a sleeping user from one or more spikes in said body motion signal.

In another embodiment of the present invention, the one or more spikes in the body motion signal and a step change in the respiration amplitude occurring simultaneously is determined to correspond to the body posture change of at least one user, and the body motion signal lacking a simultaneous step change in the respiration amplitude is determined to correspond to the body movement but no static body posture change of the at least one user. In a broader embodiment of the invention, the one or more spikes in the body motion signal and a step change in the at least one physiological property determined from the body motion signal (respiration cycle shape, respiration cycle amplitude, heartbeat cycle shape, heartbeat cycle amplitude, presence signal value) occurring simultaneously is determined to correspond to the body posture change of at least one user and the body motion signal lacking a simultaneous step change in the at least one physiological property is determined to correspond to the body movement but no static body posture change of the at least one user.

It is a further object of the present invention to provide a distributed computer system for determining the quality of sleep of at least one user using a peripheral device that comprises at least one sensor to record a body motion signal and communicate the body motion signal to a third party software application executing in a mobile subscriber terminal.

It is yet an object of the invention to provide a computer program product for determining the quality of sleep of at least one user. The computer program product comprises at least one non-transitory computer-readable storage medium having computer-readable program code portions stored therein. The computer-readable program code portions comprise instructions for performing aforesaid method of determining the quality of sleep.

A method of determining the quality of sleep of at least one user in accordance with the invention comprises:

recording a body motion signal using a peripheral device;

arranging a communication connection between the peripheral device and a mobile subscriber terminal or a computer;

communicating said body motion signal to a third party software application executing in said mobile subscriber terminal or a computer;

determining body posture changes of the at least one user based on said body motion signal and a respiration cycle amplitude signal or other signal generated by an internal organ of the user, wherein the determination of the body posture changes of at least one user is used to determine the quality of sleep.

A method of determining the quality of sleep of at least one user in accordance with the invention comprises:

recording a body motion signal using a peripheral device;

determining body posture changes of the at least one user with said peripheral device based on said body motion signal and at least one physiological property determined from the body motion signal including but not limited to respiration cycle shape, respiration cycle amplitude, heartbeat cycle shape, heartbeat cycle amplitude and/or presence signal value, wherein the determination of the body posture changes of at least one user is used to determine the quality of sleep.

A method of determining the quality of sleep of at least one user in accordance with the invention comprises:

recording a body motion signal using a peripheral device;

communicating the body motion signal to at least one network computer including but not limited to a cloud service, determining body posture changes of the at least one user with said at least one network computer based on said body motion signal and at least one physiological property determined from the body motion signal including but not limited to respiration cycle shape, respiration cycle amplitude, heartbeat cycle shape, heartbeat cycle amplitude and/or presence signal value, wherein the determination of the body posture changes of at least one user is used to determine the quality of sleep.

A distributed computer system for determining quality of sleep of at least one user is in accordance with the invention, the distributed computer system comprising:

a mobile subscriber terminal or a computer;

a peripheral device arranged to record a body motion signal and to communicate said body motion signal to a third party software application and is characterized in that, the mobile subscriber terminal or computer comprises a processor to execute the third party software application, wherein the third party application is arranged to determine body posture changes of the at least one user based on said body motion signal and a respiration cycle amplitude signal or other signal generated by an internal organ of the user, wherein the determination of the body posture changes of said at least one user is configured to be used in determining the quality of sleep.

A distributed computer system for determining the quality of sleep of at least one user in accordance with the invention comprises:

a peripheral device arranged to record a body motion signal;

said peripheral device arranged to determine body posture changes of the at least one user based on said body motion signal and at least one physiological property determined from the body motion signal including but not limited to respiration cycle shape, respiration cycle amplitude, heartbeat cycle shape, heartbeat cycle amplitude and/or presence signal value, wherein the determination of the body posture changes of at least one user is used to determine the quality of sleep.

A distributed computer system for determining the quality of sleep of at least one user in accordance with the invention comprises:

a peripheral device arranged to record a body motion signal;

said peripheral device and at least one network computer arranged to communicate the body motion signal to said at least one network computer including but not limited to a cloud service, said at least one network computer arranged to determine body posture changes of the at least one user based on said body motion signal and at least one physiological property determined from the body motion signal including but not limited to respiration cycle shape, respiration cycle amplitude, heartbeat cycle shape, heartbeat cycle amplitude and/or presence signal value, wherein the determination of the body posture changes of at least one user is used to determine the quality of sleep.

A computer program product for determining the quality of sleep of at least one user is in accordance with the invention, and the computer program product comprises at least one non-transitory computer-readable storage medium having computer-readable program code portions stored therein, said computer-readable program code portions comprising instructions for:

recording a body motion signal using a peripheral device;

arranging a communication connection between the peripheral device and a mobile subscriber terminal or computer;

communicating said body motion signal to a third party software application executing in said mobile subscriber terminal or computer and, determining body posture changes of the at least one user based on said body motion signal and a respiration cycle amplitude signal or other signal generated by an internal organ of the user, wherein the determination of the body posture changes of said at least one user is used to determine the quality of sleep.

A computer program product for determining the quality of sleep of at least one user in accordance with the invention comprises program code instructions for:

recording a body motion signal using a peripheral device;

determining body posture changes of the at least one user with said peripheral device based on said body motion signal and at least one physiological property determined from the body motion signal including but not limited to respiration cycle shape, respiration cycle amplitude, heartbeat cycle shape, heartbeat cycle amplitude and/or presence signal value, wherein the determination of the body posture changes of at least one user is used to determine the quality of sleep.

A computer program product for determining the quality of sleep of at least one user in accordance with the invention comprises program code instructions for:

recording a body motion signal using a peripheral device;

communicating the body motion signal to at least one network computer including but not limited to a cloud service, determining body posture changes of the at least one user with said at least one network computer based on said body motion signal and at least one physiological property determined from the body motion signal including but not limited to respiration cycle shape, respiration cycle amplitude, heartbeat cycle shape, heartbeat cycle amplitude and/or presence signal value, wherein the determination of the body posture changes of at least one user is used to determine the quality of sleep.

According to an embodiment of the invention, at least one static sensor and at least one dynamic sensor is integrated to the at least one sensor device of the peripheral device. The at least one sensor device is further arranged to determine presence signals and further to determine the presence of a sleeping user on a bed. A presence signal describes the user's proximity to or presence on the bed/sensor. It can be measured e.g. with dynamic sensors (e.g. piezoelectric sensors) or static sensors (e.g. capacitive sensors). It can be a binary value (present/absent) or continuous value. In fact, in one embodiment of the invention the one or more spikes in the body motion signal and a step change in the at least one physiological property determined from the body motion signal (respiration cycle shape, respiration cycle amplitude, heartbeat cycle shape, heartbeat cycle amplitude, presence signal value) occurring simultaneously is determined to correspond to at least one user entering or exiting the bed and the body motion signal lacking a simultaneous step change in the at least one physiological property is determined to correspond to the body movement but no entering or exiting of the at least one user.

Some or all of the aforementioned advantages of the invention are accrued by the integration of the static sensor and the dynamic sensor in the at least one sensor of the peripheral device. The dynamic sensor may be any sensor that can detect the motion signals (due to respiration, heartbeats, blood pressure etc.) including, but not limited to, a piezoelectric sensor and/or a piezo thin film sensor. The static sensors may include one or more sensors to detect the presence and static parameters (weight, temperature etc.) of the at least one user including, but not limited to, a strain gauge, a capacitive sensor, a proximity sensor, a thermocouple, an inductive sensor etc.

The best mode of the invention is a system wherein a peripheral device comprises an integrated sensor that includes both dynamic and static sensors, and provides the recording of body motion signal and presence signal to the third party software application of the mobile subscriber terminal. The integrated sensor provides a great advantage in accurately measuring the presence of at least one user. Further, in the best mode, the simultaneous spike in the body motion signal and the step in the respiration amplitude are interpreted as a change of body posture, whereas only spikes in body motion signal typically indicate the mere body movements. The respiration amplitude is also measured ballistographically, i.e. by force measurements in the best mode.

The respiration amplitude varies during various stages of sleep. Roughly speaking, it has been observed that it is stable when the user is awake; it is less stable in non-REM (rapid eye movement) stage, while in REM stage, the respiration is unstable. On the other hand, the body motion signal amplitude majorly depends on the posture and position of human body. It has been observed that body motion signal such as a ballistocardiographic signal has a bigger amplitude when a person sleeps on his back or on stomach than when the person sleeps on the sides. Further, it has also been seen that quick changes in the amplitude of the body motion signal such as a ballistocardiographic signal, as a step function, may correspond to the posture change. This feature is utilized in the present invention.

According to an embodiment of the invention, the third party software applications are deployed to distinguish the breathing cycles from the recorded body motion signal (raw body motion signal) and to calculate the respiration amplitude. The third party software applications are capable to detect the change in posture by analyzing the spikes of the body motion signal with respect to the simultaneous step changes in the respiration amplitude.

BRIEF DESCRIPTION OF DRAWINGS

In the following the invention will be described in greater detail with reference to exemplary embodiments in accordance with the accompanying drawings, in which.

The features of the invention illustrated above and below in the specification, are described with reference to the drawings summarized above. The reference numbers shown in the drawings may be used at one or more places to indicate the functional relation between the referenced elements. Some of the embodiments are described in the dependent claims.

DETAILED DESCRIPTION OF EMBODIMENTS

Figure 1:
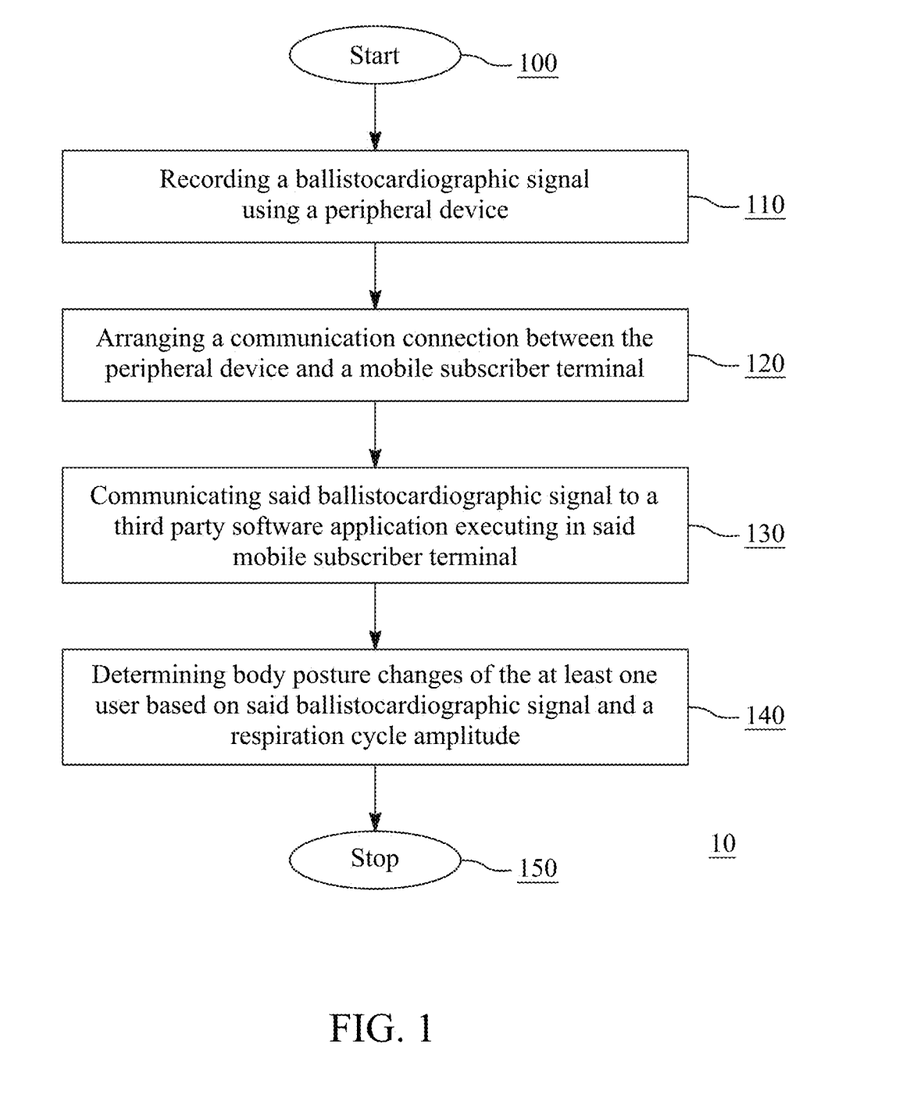
FIG. 1 demonstrates a flowchart depicting a method of determining the quality of sleep in an embodiment 10 in accordance with the invention.

As depicted in FIG. 1, an embodiment 10 of the present invention provides a method for determining the quality of sleep of at least one user. The method is initiated at step 100.

At step 110, a peripheral device records a body motion signal. The body motion signal is a combination of various signals such as signals occurring due to different mechanical body movements, heartbeats, respiration, breath cycles, blood pressure and/or other skeletal muscular movements, and presence signal etc. The peripheral device includes a sensor to record these signals as a raw body motion signal.

Thereafter at step 120, a communication connection is established between the peripheral device and a mobile subscriber terminal, to communicate the recorded body motion signal. These signals have different amplitudes and frequencies, hence one or more signals such as respiration cycle amplitude, respiration cycle shape, heartbeat cycle shape, heartbeat cycle amplitude and presence signal can be determined by deploying various algorithms.

In an embodiment, the communication connection between the peripheral device and the mobile subscriber terminal may be via any network including, but not restricted to, wireless networks such CDMA, GSM, UMTS, HSPA, EV-DO, EV-DO rev. A, 3GPP LTE, WiMAX, Wi-Fi, Bluetooth, internet, telephony, and/or wired network such as optical fibres, cables, other communication formats and combinations thereof.

Thereafter, at step 130, the peripheral device communicates the body motion signal to a third party software application executing on a mobile subscriber terminal via the communication channel. The mobile subscriber terminal may be any dedicated mobile device that includes a processor for executing the third party software application, communication hardware, a user interface and a non-volatile storage medium. In some embodiments of the present invention, the mobile subscriber terminal is a mobile phone or a tablet device. In some other embodiments the mobile subscriber terminal may be substituted by a computer.

Moving on at step 140, the third party software application determines body posture changes of the at least one user based on the body motion signal and the respiration cycle amplitude. In an embodiment, the respiration cycle amplitude is determined from the raw body motion signal. The body posture change may be determined by analyzing the spike in the body motion signal, such as a ballistocardiographic (BCG) signal, and step change of amplitude of the respiration cycle amplitude by a step recognition method. When the step change of the respiration amplitude and the spike in the raw BCG occur at the same time, the posture of the user has changed.

The detected body posture changes further help in determining the quality of sleep. Various algorithms can be deployed to analyze the body posture of the user to determine the physical and physiological condition of user. The body movements can then be analyzed to determine various sleep stages. For example in a light sleep stage the user body may show some frequent body movements such as eye movement, hand movement etc. and in deep sleep stage the user may show no mechanical body movement and respiration may be high etc.

It has been observed that the respiration amplitude varies during various stages of sleep. The respiration is stable when the user is awake; it is less stable in non-REM (rapid eye movement) stage, while in REM stage, the respiration is unstable. On the other hand, the body motion signal amplitude predominantly depends on the posture and position of human body. It has also been observed that respiration signal has a bigger amplitude when a person sleeps on his back or on stomach than when he sleeps on either side. Further, it is examined that the quick changes in the amplitude of respiration signal, as a step function, may correspond to the posture change. This feature is utilized in the present invention and in this way the quality of sleep may be analyzed.

Various techniques and/or algorithms can be deployed to extract aforementioned signals and/or parameters from the body motion signals. In order to identify the ballistic effect of cardiac activity and the pushing effect of respiratory activity, one or more signal processing techniques, such as iterative analysis and adaptive filtering can be utilized in the embodiment. The presence signals are basically the signals generated due of the presence of user in the proximity of the at least one sensor.

The algorithms of the third party software application are capable of distinguishing individual breathing cycles, respiration and presence signals from the body motion signal. The respiration amplitude signal, i.e. the change of the amplitude, during the night is analyzed with a simple step recognition method and the times of the recognized step changes from the signal are recorded. At the same time, it is possible to detect absence of the user from the bed. During the absence of user the amplitude of body motion signals will be significantly low and/or static over the time. This will indicate that the user is not sleeping and/or not in the proximity of the at least one sensor.

The method is terminated at step 150.

It should be noted that any features, phases or parts of embodiment 10 can be freely permuted and combined with any of the embodiments 20, 21, 30, 40, 41 and/or 50 in a combination of two or more embodiments in accordance with the invention.

Figure 2:
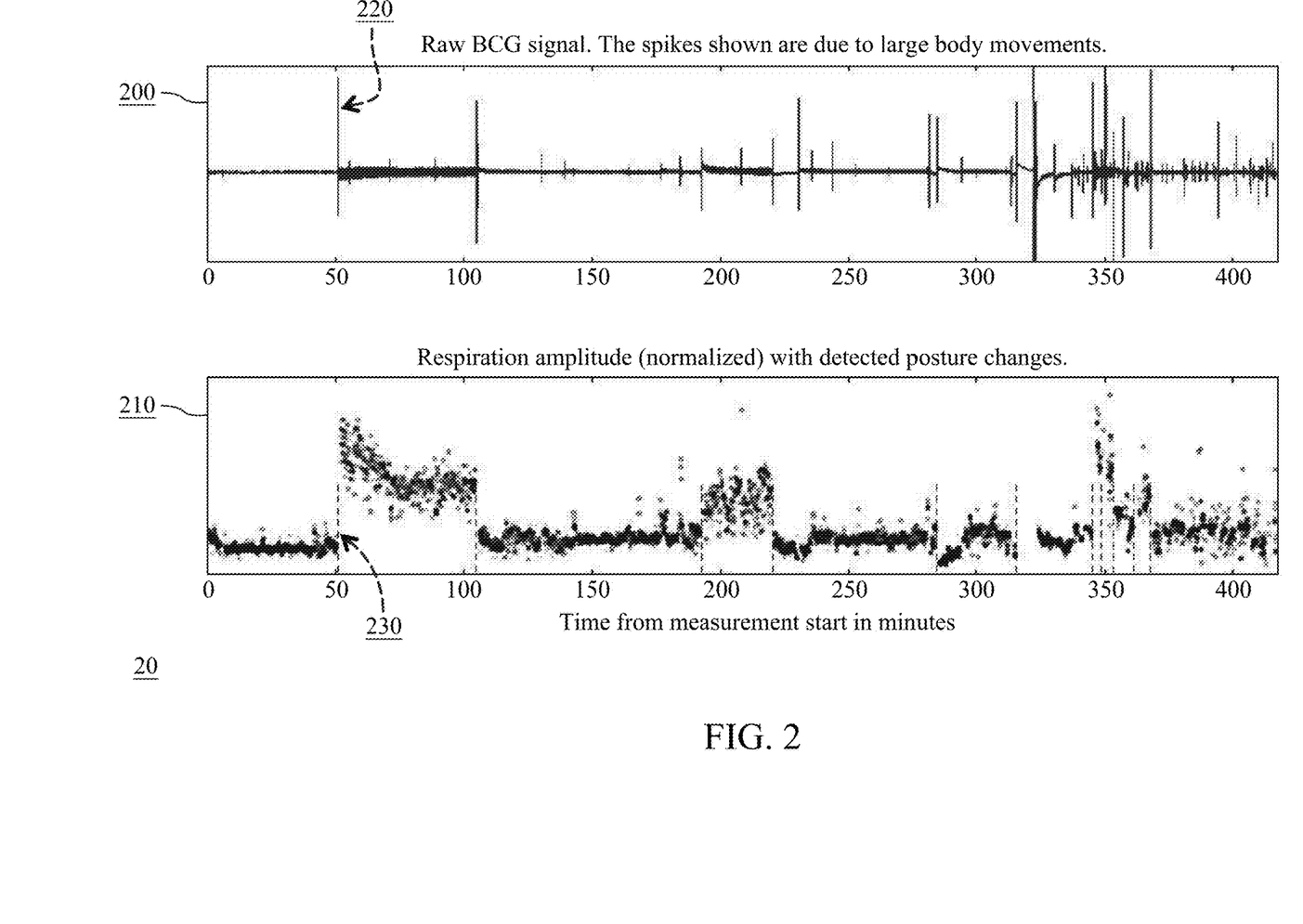
FIG. 2 demonstrates a graphical representation of the body motion signal and the respiration cycle amplitude in an embodiment 20 of the invention.
Figure 2B:
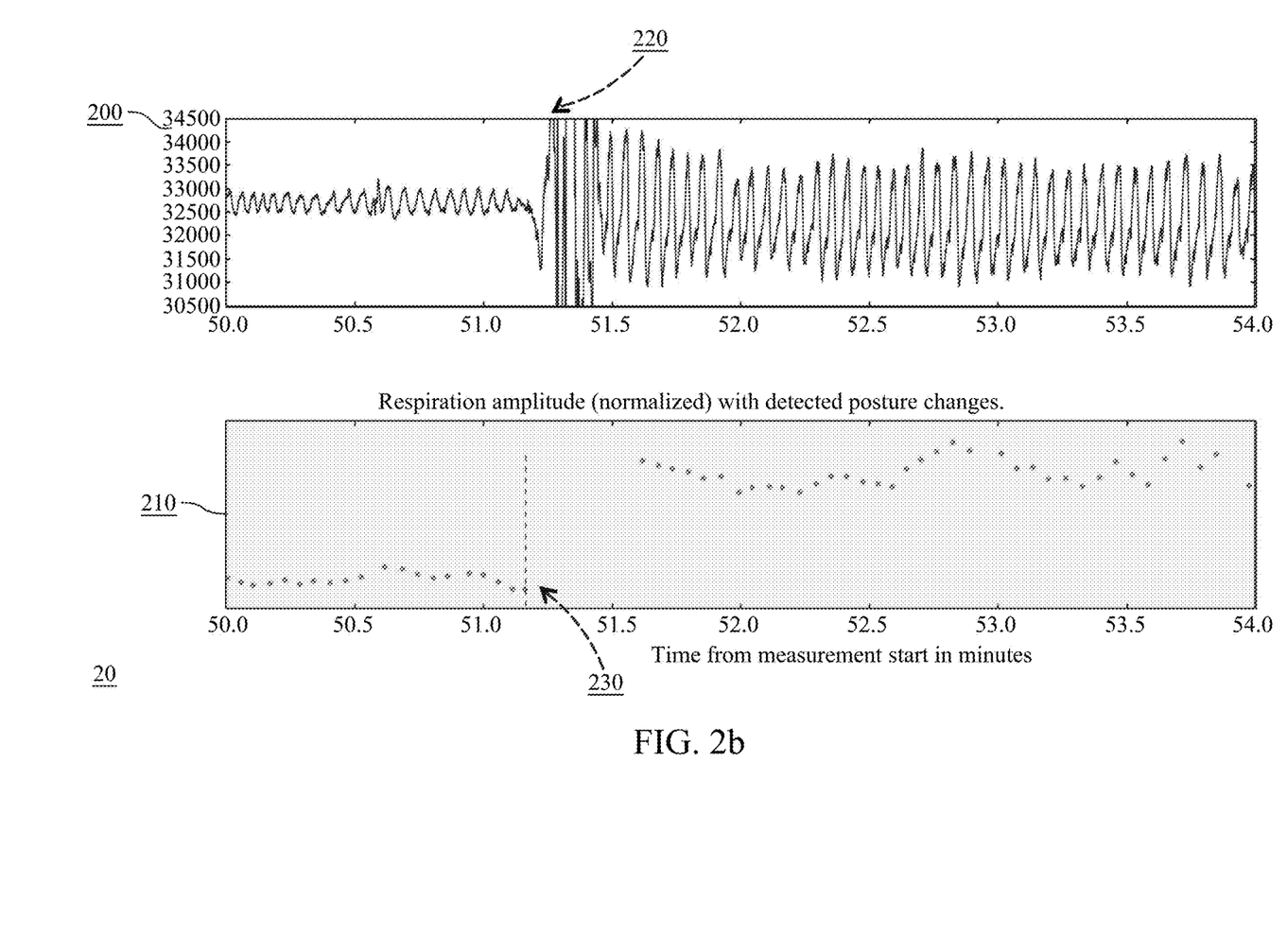
FIG. 2b demonstrates a graphical representation of the body motion signal and the respiration cycle amplitude in an embodiment 20 of the invention.

Moving on, FIG. 2 demonstrates a graphical representation of a body motion signal 200 and a respiration cycle amplitude 210, in accordance with an embodiment of the invention. An embodiment 20 of present invention provides a way to analyze these signals for determining the static body posture change and/or body movements. FIG. 2*b* demonstrates a graphical representation of a body motion signal 200 and a respiration cycle amplitude 210, in such a way that the signals are the same as in FIG. 2, but the temporal range in the figure is shorter.

In FIG. 2 and FIG. 2*b*, in the top chart, there is shown the raw body motion signal 200, which has been recorded during one night and the respiration cycle amplitude 210 (bottom of the chart) that has been determined from the body motion signal 200. Various algorithms can be deployed to detect the spikes caused by body movements, and further in between the spikes, there are level plateaus from which the breathing cycles can be easily detected. In the figure the vertical dotted lines show the detected changes of body posture. By comparing the raw body motion signal 200 and the respiration cycle amplitude 210, it is possible to detect a change in body posture. The change in body posture is determined when the spike in body motion signal 200 occurs concurrently with the step change in amplitude of the respiration amplitude cycle 210.

As shown in FIG. 2, there is a simultaneous occurrence of the spike 220 and the step change 230 at time 51 and at time 104 or so. This indicates that user has changed the posture at time 51 and at time 104. Further, it has been seen that almost no step change and/or very low amplitude spikes are detected in the body motion signal 200 between 100 to early 200 minutes, the third party software application may deduce that the user is in deep sleep during this period and further, the frequent change in the posture of the at least one user has been recorded around 350 minutes which indicates that the user is in light sleep or no sleep during this period. Thus, in this way the third party software application will determine the quality of sleep of the at least one user.

It should be noted that any features, phases or parts of embodiment 20 can be freely permuted and combined with any of the embodiments 10, 21, 30, 40, 41 and/or 50 in a combination of two or more embodiments in accordance with the invention.

Figure 2C:
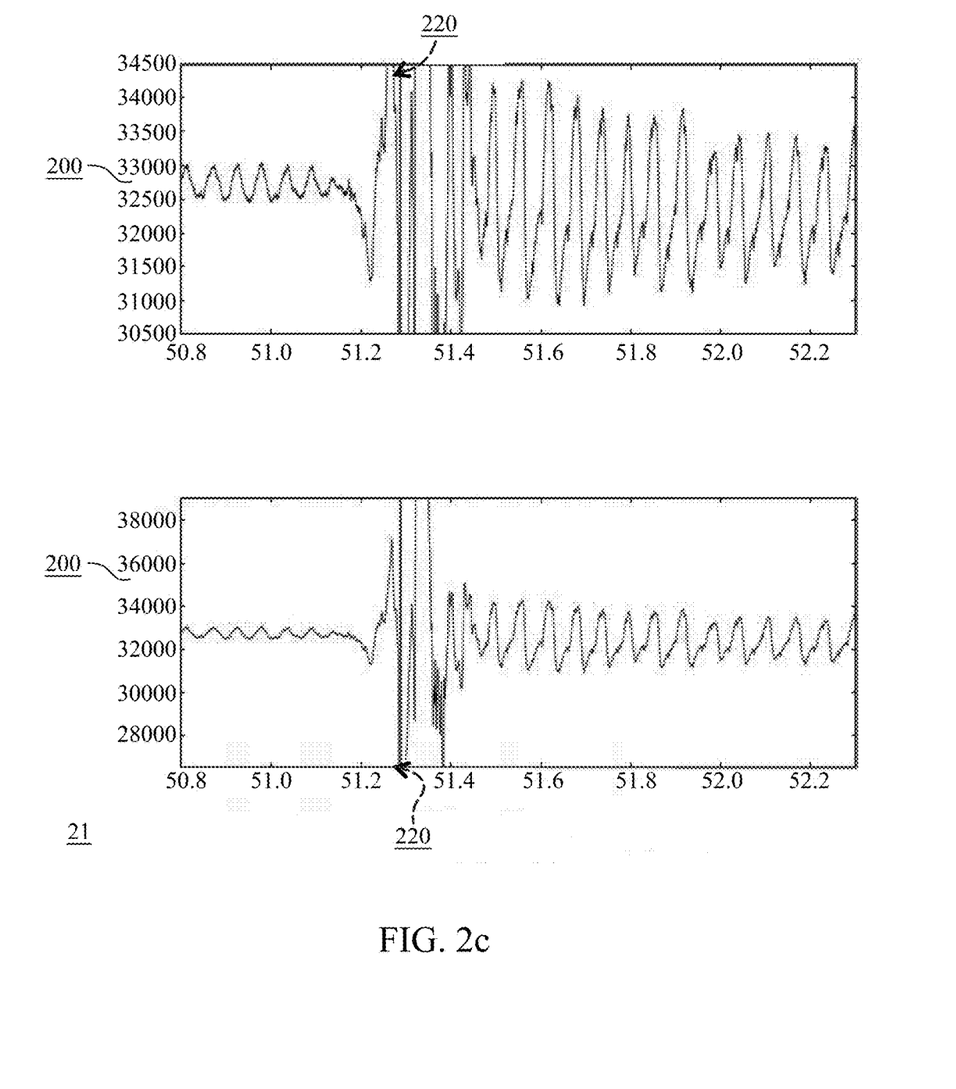
FIG. 2c demonstrates a graphical representation of the body motion signal and the respiration cycle shape in an embodiment 21 of the invention.

FIG. 2*c* demonstrates a graphical representation of a body motion signal 200 in accordance with an embodiment of the invention. In the figure, there is shown a 1.5-minute excerpt of the raw body motion signal 200. There is a simultaneous occurrence of the spike 220 (the spike occurring between 51.2 minutes and 51.5 minutes) and a step change of the respiration cycle shape and respiration cycle amplitude in the raw body motion signal 200. This indicates that user has changed the posture between 51.2 minutes and 51.5 minutes. Two zooming levels of the body motion signal 200 are provided in FIG. 2c, so that it can be recognized that in addition to the evident step change in respiration cycle amplitude, there is a step change also in the respiration cycle shape.

The third party software application algorithm is configured to distinguish the static body posture change and/or body movements of the at least one user. It may utilize the step recognition method for analyzing the body motion signal 200. In this method, basically, the third party software application recognizes the one or more spikes in the body motion signal 200 and a concurrent step change in the respiration cycle amplitude 210. These concurrent events are determined to mean that posture has changed. Various techniques can be utilized for step recognition. The step recognition may utilize one or more statistical and/or signal processing algorithms.

In one aspect of the present invention, the simultaneous occurrence of the one or more spikes in said body motion signal and a step change in the respiration amplitude is considered as the body posture change of the at least one user. The combination of one or more spikes in said body motion signal lacking a simultaneous step change in the respiration amplitude is considered as a mere body movement without static body posture change of the at least one user. Thus it is clear that the spikes of significant threshold in body motion signal may refer to the body movements but not necessarily posture change. This is simply because body movements do not always lead to the body posture change.

It should be noted that any features, phases or parts of embodiment 21 can be freely permuted and combined with any of the embodiments 10, 20, 30, 40, 41 and/or 50 in a combination of two or more embodiments in accordance with the invention.

Figure 3:
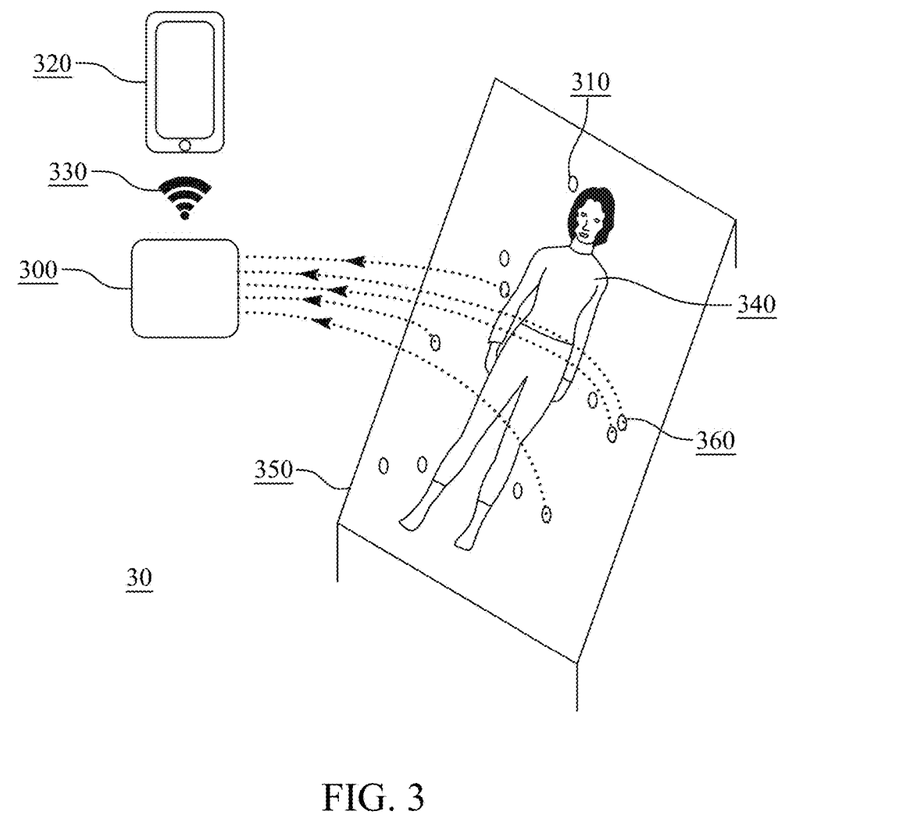
FIG. 3 demonstrates an embodiment 30 depicting a sleeping user 340, sensor with both dynamic 310 and static 360 sensors integrated, a mobile subscriber terminal 320 with a third party software application in accordance with the invention.

FIG. 3 depicts a distributed computer system for determining the quality of sleep of at least one user in accordance with the invention. In an embodiment 30 of the present invention, the posture of a sleeping user 340 is detected using a peripheral device 300. The peripheral device 300 is in a communication connection 330 with the mobile subscriber terminal 320. The peripheral device 300 includes at least one sensor to record the body motion signal of a user.

In one embodiment of the present invention the peripheral device includes a plurality of sensors. In some embodiments the plurality of sensors may be dynamic sensors 310 such as piezoelectric sensor and/or piezo thin film sensors. In other embodiments the sensors may be static sensors 360 such as one or more of the following: a strain gauge, a capacitive sensor, a proximity sensor, a thermocouple, an inductive sensor etc. In another embodiment of the present invention, the peripheral device includes both the static sensors 360 and the dynamic sensors 310.

In some aspects of the present invention, the measurement of the cardiac activities through ballistocardiography utilizes one or more piezoelectric sensors. A piezoelectric sensor can have a crystal and when the crystal gets deformed under a mechanical load, the crystal starts re-distribution of its electric charge to the surroundings. This piezoelectric effect can be used to measure, e.g., pressure, acceleration, strain or force.

A piezoelectric sensor installed at a surface of a deformable object, such as a mattress, can be used for measuring the amount of deformation of the object when experiencing a mechanical load. The piezoelectric measurement has superior sensitivity for dynamic phenomena, so it is the primary method for vital sign detection and posture detection. Even though having no significant static presence detection capabilities, the variability of the piezoelectric output is also used as a presence indicator in some embodiments, since the human body is never completely still.

In an embodiment of the present invention, the strain gauge may be used to detect the state of physical motion of the user on the bed, by detecting the static deflection of the sensor caused by the presence of the person. The strain gauge integrated into the piezo sensors may be utilized to measure the vibration signals occurring due to the respiration and/or other body movements of the user. In some embodiments, the strain gauge sensor is arranged on the elastic fabric of user mattress in such a way that movements of the user's chest due to heartbeat and/or respiration lead to a fluctuating strain gauge signal. The direct signal originating from the strain gauge in order to record heartbeat and respiration may be communicated to the mobile third party software application.

In another embodiment of the present invention, two capacitive load cells may be mounted at/on near the top and bottom middles of the user's bed to detect the presence of the user by detecting an increment in the weight on the bed.

In some further embodiments of the present invention, the capacitive proximity sensor film may be used to detect the presence of user in the proximity of one or more sensors. For example, the presence of the user alters the electric flux field lines of at least one capacitive proximity sensor films which is detected. Typically the electric flux density increases when the user lies on top of the capacitive proximity sensor film.

The presence of the user may also be indirectly determined from the presence of the mobile subscriber terminal, for example by determining the location of the mobile using WiFi, GPS, BlueTooth, iBeacon, GSM, CDMA, 3G, 4G, and/or any other cellular technology.

In further embodiments of the present invention, the one or more sensors of sensor device are enabled to measure temperature differences between the one or more thermocouples and the sensor device. The temperature difference between the terminals of thermocouples indicates presence of one user, or more than one user.

In some aspects, the piezoelectric sensor and/or a piezo thin film sensors are arranged on the elastic fabric of a user mattress 350 in such a way that movements of the user's chest due to heartbeat and/or respiration lead to a mechanical stress on the thin film of the piezoelectric sensors. The direct signal originating from these sensors to monitor heartbeat and respiration may be communicated to the mobile third party software application.

In an embodiment, the peripheral device 300 may be in form of a thin IC device and can be placed on the user's bed and/or it may be adapted to be located at a remote location with communication enabled with the one or more sensors. In some embodiments, the peripheral device 300 can be in the form of a thin lace or strip of soft fabric so that the user may find it convenient to easily sleep on it.

In an embodiment of the present invention, the peripheral device 300 includes a plurality of sensors that are placed at multiple sensitive areas for determining the presence signals, and/or further determining the position of the person on the bed. The plurality of sensors may determine how many times the user exists from the bed, how many times user changes his position, at what time user usually changes his position or at what time the user sleep stage changes etc. In some embodiments of the present invention, the static sensors sense the user position and/or dimension on the bed and dynamic sensors sense the respiration, heart rate etc. Using the collaborated data of static and dynamic sensors, the third party algorithm such as the one of the Beddit App or the like may detect and/or analyze one or more of the following: sleep stage of a user, sleeping time of a user, user presence on bed, presence of more than one user on the bed etc.

It should be noted that any features, phases or parts of embodiment 30 can be freely permuted and combined with any of the embodiments 10, 20, 21, 40, 41 and/or 50 in a combination of two or more embodiments in accordance with the invention.

Figure 4A:
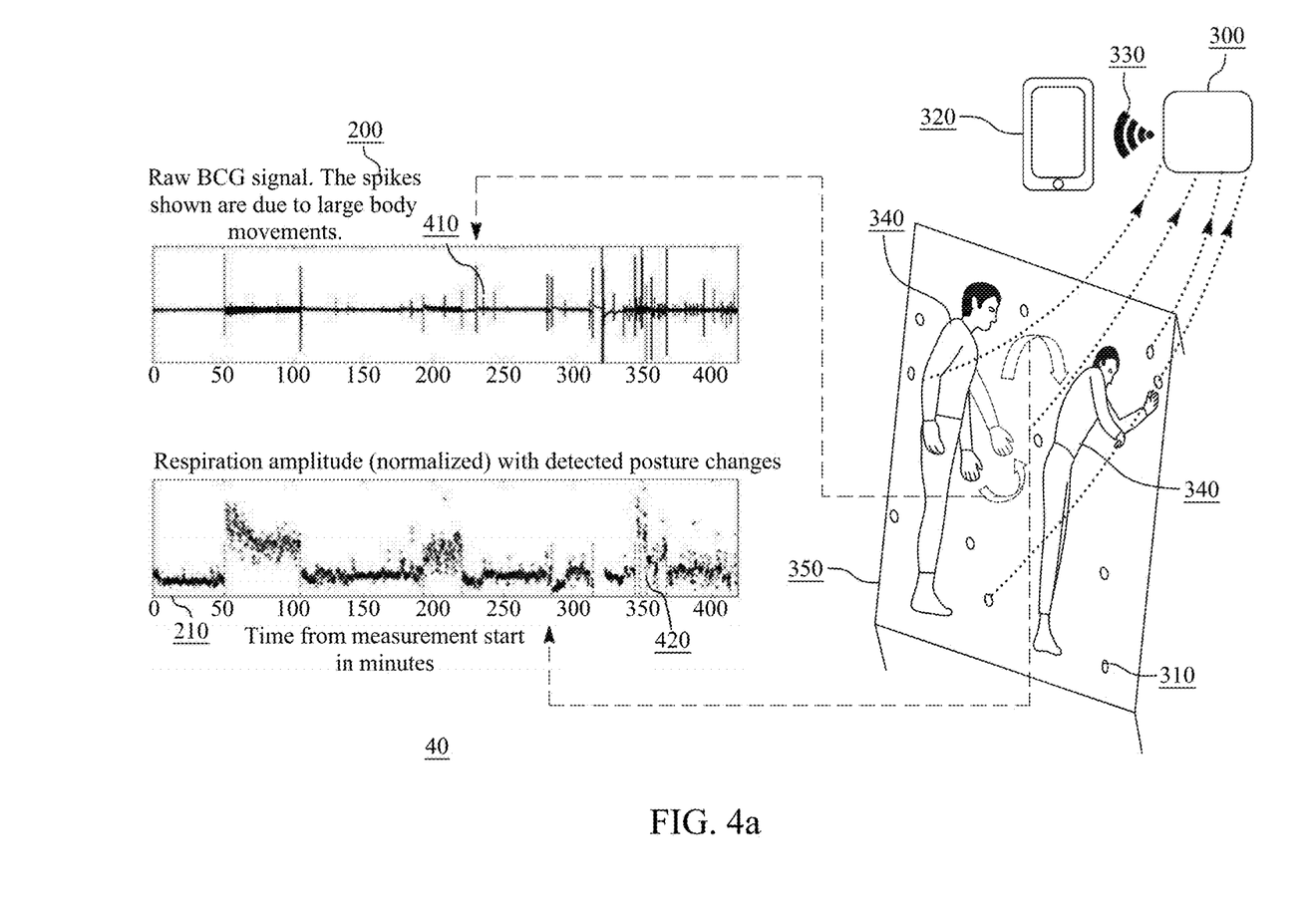
FIG. 4a demonstrates an embodiment 40 depicting a sleeping user 340, body movements and posture change of the sleeping user in accordance with the invention.

FIG. 4a demonstrates a system for determining the quality of sleep according to an embodiment 40 of the present invention. In the embodiment, the peripheral device 300 records the body motion signal of the sleeping user 340 in order to detect the body movements and posture changes of the sleeping user 340. The user 340 is sleeping on the mattress 350. In the embodiment a plurality of sensors are integrated into the mattress 350 for detecting the presence of the user 340 and for recording the body motion signal 200. The static posture change and the body movements may be detected by analyzing the body motion signal 200 and the respiration cycle amplitude 210 by a third party software application executing on the mobile subscriber terminal 320.

The spikes of the body motion signals 200 represent the skeletal muscle movements in the user body. As shown in the figure, when the user 340 moves a hand while sleeping, the spike 410 corresponding to that movement occurs in the body motion signal 200 without any step change in the respiration amplitude signal 210 at that time.

This is in stark contrast to what happens e.g. at 350 minutes when the user 340 changes his posture, a spike in body motion signal 200 with simultaneous step change 420 in respiration amplitude signal 210 is detected. The amplitude of the spikes shows the strength of body movements. The larger amplitude of spikes, the larger the body movement, while lower amplitude spikes show a smaller movement in the user's body. The static posture of the user 340 may be detected using one or more static sensors.

It should be noted that any features, phases or parts of embodiment 40 can be freely permuted and combined with any of the embodiments 10, 20, 21, 30, 41 and/or 50 in a combination of two or more embodiments in accordance with the invention.

Figure 4B:
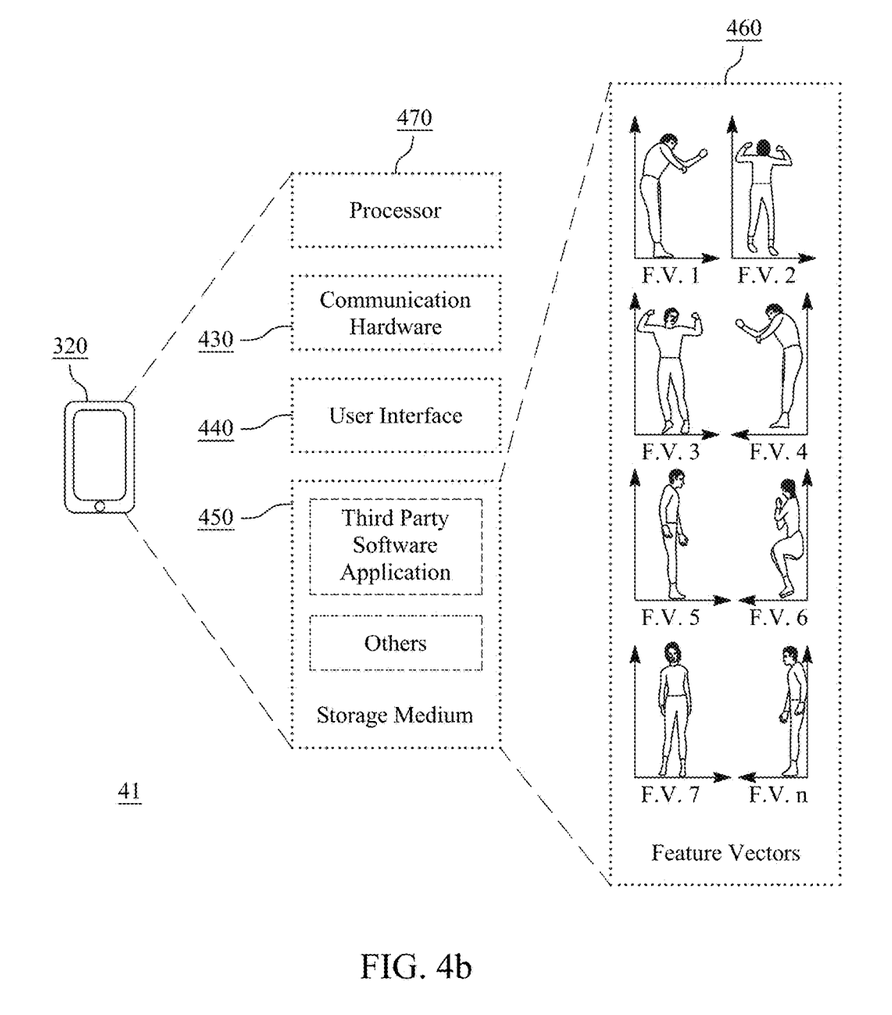
FIG. 4b demonstrates an embodiment 41 depicting a mobile subscribers terminal 320 comprising a storage medium 450 having plurality of body postures 460 and feature vectors associated with each body posture in accordance with the invention.

In one embodiment 41 as depicted in FIG. 4b, the mobile subscriber terminal 320 includes communication hardware 430, user interface 440, a storage medium 450 and a processor 470. The storage medium 450 includes a third party software application and a memory to store a plurality of body postures 460 and feature vectors (F.V. 1, F.V. 2, ... F.V. n) associated with each body posture. The processor 470 is configured to execute the third party software application. Further in some embodiments the storage medium 450 includes a third party software application configured to detect the body posture of the user based on the physiological properties of the user determined from the body motion signal, such as any of the following: respiration cycle shape, respiration cycle amplitude, heartbeat cycle shape, heartbeat cycle amplitude and/or presence signal value.

In an exemplary embodiment, the feature vector 1 (F.V. 1) may correspond to the body posture when the user sleeps on his left side. The feature vector 2 (F.V. 2) may correspond to the body posture when the user sleeps on his stomach. The feature vector 3 (F.V. 3) may correspond to the body posture when the user sleeps on his back with arms up (generally called starfish posture). The feature vector 4 (F.V. 4) may correspond to the body posture when the user sleeps on his right side. The feature vector 5 (F.V. 5) may correspond to the body posture when the user sleeps on his left sides with arms in their sides. The feature vector 6 (F.V. 6) may correspond to the body posture when the user sleeps on his right sides with folded legs. The feature vector 7 (F.V. 7) may correspond to the body posture when the user sleeps on his back with down arms. The feature vector n (F.V. n) may correspond to the body posture when the user sleeps on his right side with down arms on their sides. Many other feature vectors can be assigned for the body postures of the user in accordance with the invention.

In one embodiment, the feature vector can be assigned on the basis of user's dimensions on the bed. Then each feature vector may be associated with a sleep parameter, for example if the user is sleeping with folded leg and in curl posture, the third party software application may assume that the user is suffering from anxiety.

The human body postures are classified in FIG. 4b in a 2*4 posture matrix, each associated with a feature vector. The posture classification may be performed by a variety of methods. Some postures may be classified through support vector machines (SVM) or some other suitable classifier such as artificial neural network in accordance with the invention. The posture of the at least one user can be determined by classifying the feature vectors. In the embodiment, a classifier is arranged to know how the features of body motion signal are known to look like in different user body postures based on reference data in data storage. The parameters of the feature vectors include the at least one physiological property determined from the body motion signal (respiration cycle shape, respiration cycle amplitude, heartbeat cycle shape, heartbeat cycle amplitude, presence signal value).

In the embodiment, a posture reference data may be accessible in online and/or off-line mode, and the posture reference data may include one or more sets of posture according to each user of the distributed computer system. In the posture reference data a feature vector may be assigned to the each body motion and/or posture. When a posture change is detected, a camera may capture an image or a recording module records the posture statistics and may communicate the data to the mobile subscriber terminal 320. The classifier may utilize various techniques to compare the feature vector with the posture recorded by the distributed computing system to calculate a degree of similarity.

Further, the third party software application is arranged to store images and/or data of body postures of the at least one user during sleep into data storage, and display said images and/or data later on screen of said mobile subscriber terminal. The images may be real time still images and/or motion pictures. The classifier and/or the third party software application may be arranged to classify one or more users according to their physical statistics such as height, weight etc. In this way the classifier and/or the third party software application will be able to recognize the one or more users and may record the posture data corresponding to the each user.

It should be noted that any features, phases or parts of embodiment 41 can be freely permuted and combined with any of the embodiments 10, 20, 21, 30, 40 and/or 50 in a combination of two or more embodiments in accordance with the invention.

Figure 5:
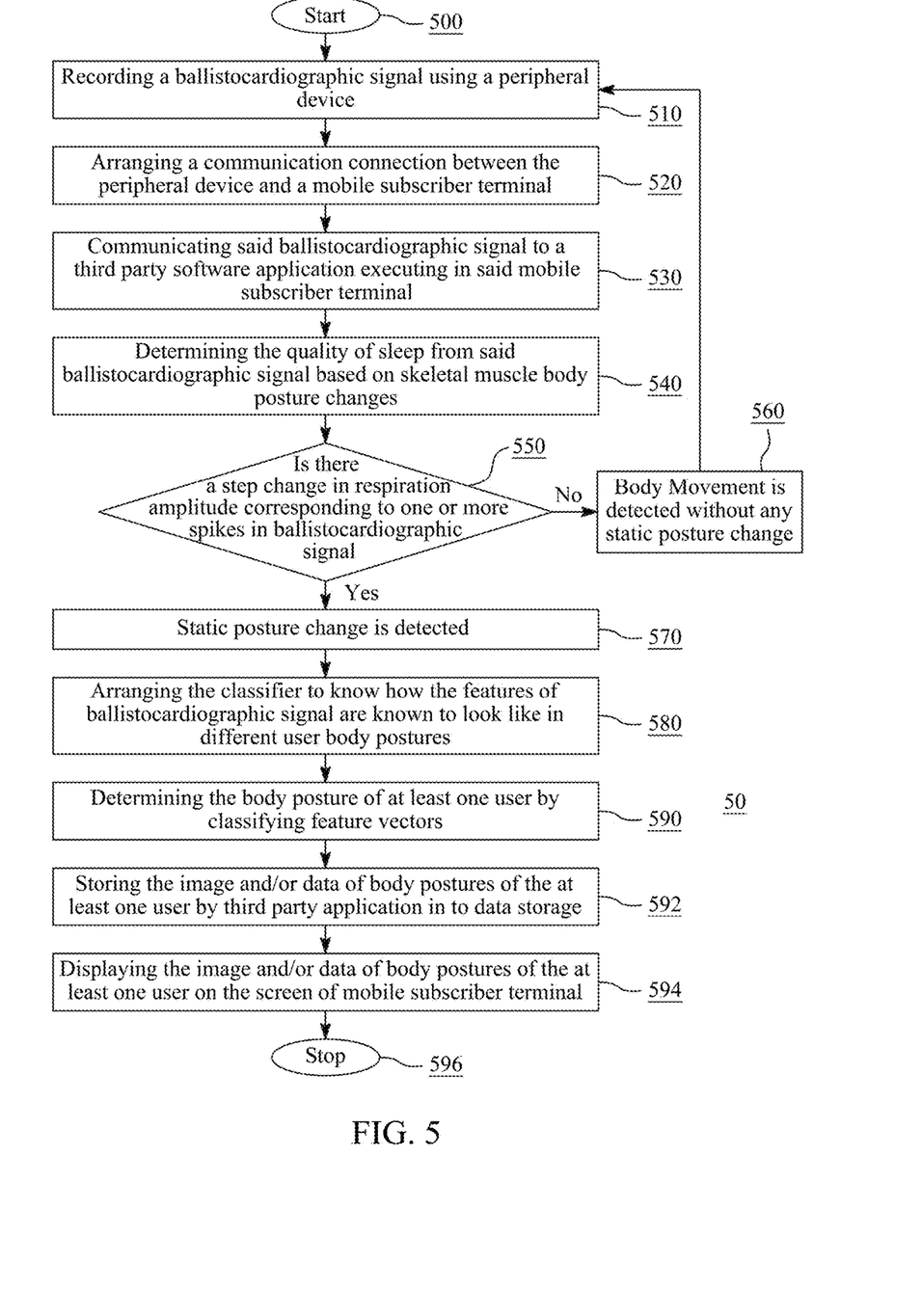
FIG. 5 demonstrates a flowchart depicting a method of communicating the quality of sleep in an embodiment 50 in accordance with the invention.

Referring to FIG. 5, an embodiment 50 of the present invention provides a method of determining the quality of sleep of at least one user.

The method is initiated at step 500. At step 510, the at least one sensor of the peripheral device records the body motion signal, which is a ballistocardiographic signal in this case. At step 520, a communication connection between the peripheral device and the mobile subscriber terminal is arranged to communicate the said body motion signal to the third party software application executing on the mobile subscriber terminal.

Further, in step 530, the peripheral device communicates the body motion signal to a third party software application. The third party application is arranged to determine one or more parameters from the signals such as respiration cycle shape, respiration cycle amplitude, heartbeat cycle shape, heartbeat cycle amplitude and the presence signal etc.

Thereafter at step 540, the quality of sleep is determined from said body motion signal based on skeletal muscle body posture changes. The posture change may be detected by comparing the simultaneity of spikes in the body motion signal and the step change in the respiration cycle amplitude.

At step 550, the third party software application checks if there is any step change in respiration amplitude corresponding to one or more spikes in body motion signal at a time.

At step 560, it is checked if there is a simultaneous step change in respiration amplitude with the one or more spikes in body motion signal. If there is none, then the third party software application assumes it is only a body movement and returns to step 510.

If there is a simultaneous step change in respiration amplitude with the one or more spikes in body motion signal, the third party software application will assume it as the static posture change of at least one user in step 570.

Furthermore at step 580, the third party software application arranges the classifier software (such as support vector machine (SVM) or artificial neural network) to know how the features of body motion signal are known to look like in different user body postures. Thereafter, at step 590, the body posture of at least one user by classifying feature vectors is determined.

At step 592, the image and/or data of body postures of the at least one user by third party application is stored to data storage. Subsequently, at step 594 the image and/or data of body postures of the at least one user is displayed on the screen of the mobile subscriber terminal. In some embodiments of the invention the postures are displayed on the mobile subscriber terminal screen as a video, fast-forward video, or slow-forward video or any other video.

The method is terminated at step 596.

It should be noted that any features, phases or parts of embodiment 50 can be freely permuted and combined with any of the embodiments 10, 20, 21, 30, 40, and/or 41 in a combination of two or more embodiments in accordance with the invention.

In some other embodiments of the invention, the mobile third party software application may be configured to generate sleep reports of one or more users. The mobile third party software application may also communicate the user sleep reports to one or more centralized server or hub, which may be located at e.g. hospitals and/or clinics. The mobile third party software application can also be configured to share user sleep data with one or more mobile applications for further analysis.

Some or all of the aforementioned advantages of the invention are accrued by the integration of the static sensor 310 and the dynamic sensor 360 in the at least one sensor of the peripheral device 300. The dynamic sensors 360 may be any sensor that can detect the motion signals (due to muscles, heartbeats, respiration etc.) including but not limited to a piezoelectric sensor and/or a piezo thin film sensors. The static sensors 310 may include one or more sensors to detect the presence and static parameters (weight, temperature etc.) of the at least one user including but not limited to a strain gauge, a capacitive sensor, a proximity sensor, a thermocouple, an inductive sensor etc.

The best mode of the invention is the system wherein a peripheral device 300 comprises an integrated sensor that includes both dynamic 360 and static sensors 310, and provides the recording of body motion signal 200 and presence signal to the third party software application of the mobile subscriber terminal 320. The integrated sensor provides a great advantage in accurately measuring the presence of at least one user 340. Further, in the best mode, the simultaneous spike in the body motion signal 200 and the step in the respiration amplitude 210 are interpreted as a change of body posture, whereas only spikes in body motion signal 200 typically indicate the mere body movements. Further, in another preferred mode of the invention, the mobile third party software application is enabled to determine the quality of sleep of more than one user using the one or more physical statistics detected by the sensor elements. The combination of above mentioned sensor elements used in determination of the one or more physical statistics enables the distributed computer system to determine the posture of more than one user more precisely. Further, various algorithms may be deployed to analyze the posture of more than one user and to determine the physical and physiological conditions (such as whether and to what extent the user is relaxed, in stress, in fever etc.) using the combination of various sensing data such as (respiration, breath, blood pressure, posture and position etc.).

It should specifically be noted that the respiration amplitude signal may be replaced by a measured signal of respiration cycle shape, respiration cycle amplitude, heartbeat cycle shape, heartbeat cycle amplitude and/or presence signal, and in an equal manner the concurrency of spike or step change in the two signals (body motion signal+physiological property signal extracted therefrom) will signify body posture change of user.

An embodiment of the invention provides a computer program product for recording and analyzing the body motion signal of at least one user by the computing device. The computer device includes at least one non-transitory computer-readable storage medium having computer readable program code portions stored therein. The said computer-readable program code portions comprise instructions to implement the aforementioned method of determining the quality of sleep. The exemplary methods described above are typically stored on a computer readable storage medium, which may be any device that can store code for use by a computer system, mobile computer system and/or other computer systems. The computer-readable storage medium includes, but is not limited to volatile memory, non-volatile memory, magnetic and optical storage devices such as disk drives, magnetic tape, CDs compact discs, DVDs digital versatile discs or digital video discs, or other media capable of storing program code now known or later developed.

Furthermore, methods described herein can be embossed on hardware modules or apparatus. These modules or device may include, but are not limited to, an application-specific integrated circuit ASIC chip, a field-programmable gate array FPGA, a dedicated or shared processor that executes a particular software module or a piece of code at a particular time, and/or other programmable-logic devices known or later developed. When the hardware modules or apparatus are activated, they perform the methods and processes included within them.

It should be noted that any features, phases or parts of any embodiment 10, 20, 21, 30, 40, 41 and/or 50 can be freely permuted and combined with any of the embodiments 10, 20, 21, 30, 40, 41 and/or 50 in a combination of two or more embodiments in accordance with the invention.

Various alternatives and modifications can be made to the aforementioned embodiments. It should further be noted that the embodiments described above may be used in both ways either individually or two or more embodiments may be combined according to the user's need. The embodiments should not be limited by their names. For example, the construction of any sensors, e.g. proximity sensors may take on any of a variety of forms, including, but not limited to, an ultrasonic sensor, a capacitive sensor, a photoelectric sensor, an inductive sensor, a camera, a light sensor such as a photo detector, a sound sensor such as a microphone, a mechanical sensor and/or the combination(s) thereof.

Further, another preferred mode of the invention is where the peripheral device 300 includes one or more sensors being integrated with the one or more sensor elements including but not limited to the strain gauge, capacitive sensors, proximity sensors, thermocouples, inductive sensors, excited piezo film and their combination thereof. In the preferred embodiment, the peripheral device can be integrated in to the mattress 350 of user.

The invention has been explained before primarily with reference to the embodiment wherein the following phases occur:
1. Recording using a peripheral device,
2. Communicating the signal to a third party software application executing in a mobile subscriber terminal,
3. Determining body posture changes in the mobile subscriber terminal. This is believed to be the best mode in terms of network topology.

However, the invention is not limited to this network topology or these phases. In one alternative both the recording of the signal and the determination of the body posture changes are done on the peripheral device. In another embodiment the signal is recorded at the peripheral device, then communicated to a server in a cloud service, and the body posture changes are determined in the cloud service.

The foregoing detailed description will provide those skilled in the art with precise disclosure for implementing an exemplary embodiment of the invention, it being understood that various changes may be made in the methods and order of steps described in an exemplary embodiment without departing from the scope of the invention as set forth in the appended claims and their legal equivalents. The invention has been explained above with reference to the aforementioned embodiments. However, it is clear that the invention is not only restricted to these embodiments, but includes all possible embodiments within the spirit and scope of the inventive thought and the following patent claims.

REFERENCES

US 2010/0016685 A1, "Separating Cardiac Signal And Respiratory Signal From Vital Signs", Pedro Miguel FONSECA et al, 2012
US 2007/0156060 A1, "Real-Time Video Based Automated Mobile Sleep Monitoring Using State Inference", Miguel Cervantes, 2005
Quantified sleep: new gadget from China wants in your bed Nov. 27, 2014 18:14, Paul Bischoff (http://www.techinasia.com/author/paulbischoff/) 10:28 am on 19 Nov. 2014

The invention claimed is:

1. A method of determining quality of sleep of at least one user, the method comprising:
   using a peripheral device to record a body motion signal of the at least one user, the peripheral device comprising a static sensor and a dynamic sensor;
   using the peripheral device to establish a communication connection between the peripheral device and a mobile phone;
   communicating the body motion signal from the peripheral device to the mobile phone; and
   using the mobile phone to:
      determine respiration amplitudes from the body motion signal;
      detect a change in the body motion signal in a given window of time;
      detect an increase or an absence of an increase in a respiration cycle amplitude in the given window of time, wherein the respiration cycle amplitude is an average of the respiration amplitudes taken over the given window of time;
      determine body posture changes of the at least one user when the change in the body motion signal and the increase in the respiration cycle amplitude are detected simultaneously;
      determine body movements of the at least one user when the change in the body motion signal and the absence of the increase in the respiration cycle amplitude are detected simultaneously; and
      determine the quality of sleep of the at least one user based on occurrences of the determined body posture changes and the determined body movements.

2. The method as claimed in claim 1, wherein the body posture changes are further determined using a change in one or more of signals determined from the body motion signal, the signals include:
   a respiration cycle shape, a heartbeat cycle shape, a heartbeat cycle amplitude, and a value of presence signals.

3. The method as claimed in claim 1, wherein the determination of the body posture changes of the at least one user includes:
   classifying the body motional signal to feature vectors, the feature vectors associated with body postures.

4. The method as claimed in claim 1, further comprising:
   capturing one or more images and data of body postures of the at least one user during sleep;
   storing the one or more of images and the data of the body postures of the at least one user into a data storage; and
   displaying the one or more of the images and the data of the body postures on a screen of the mobile phone.

5. The method as claimed in claim 1, wherein the dynamic sensor is one or more of a piezoelectric sensor and a piezo thin film sensor, and
   the static sensor is one or more of a strain gauge, a capacitive sensor, a proximity sensor, a thermocouple, and an inductive sensor.

6. The method as claimed in claim 1, wherein the peripheral device comprises a plurality of sensors placed at multiple sensitive areas to determine one or more of (a) presence signals and (b) a position of the at least one user on a bed.

7. A distributed computer system to determine quality of sleep of at least one user, the distributed computer system comprising:

a mobile subscriber terminal comprising a processor;
a peripheral device configured to record a body motion signal and to communicate the body motion signal to the mobile subscriber terminal, the peripheral device comprising at least one static sensor and at least one dynamic sensor,
wherein the mobile subscriber terminal:
determines respiration amplitudes from the body motion signal;
detects a change in the body motion signal in a given window of time;
detects an increase or an absence of an increase in a respiration cycle amplitude in the given window of time, wherein the respiration cycle amplitude is an average of the respiration amplitudes taken over the given window of time;
determines body posture changes of the at least one user when the change in the body motion signal and the increase in the respiration cycle amplitude are detected simultaneously;
determines body movements of the at least one user when the change in the body motion signal and the absence of the increase in the respiration cycle amplitude are detected simultaneously; and
determines the quality of sleep of the at least one user based on occurrences of the determined body posture changes and the determined body movements.

8. The distributed computer system as claimed in claim 7, wherein the body posture changes are further determined using a change in one or more of signals determined from the body motion signal, the signals include:
a respiration cycle shape, a heartbeat cycle shape, a heartbeat cycle amplitude, and a value of presence signals.

9. The distributed computer system as claimed in claim 7, wherein the determination of the body posture changes of the at least one user includes:
classifying the body motion signal to feature vectors, the feature vectors associated with body postures.

10. The distributed computer system as claimed in claim 7, further comprising:
capturing one or more images and data of body postures of the at least one user during sleep;
storing the one or more of images and the data of the body postures of the at least one user into a data storage; and
displaying the one or more of the images and the data of the body postures on a screen of the mobile subscriber terminal.

11. The distributed computer system as claimed in claim 7, wherein the at least one dynamic sensor is one or more of a piezoelectric sensor and a piezo thin film sensor.

12. The distributed computer system as claimed in claim 7, wherein the at least one static sensor is one or more of a strain gauge, a capacitive sensor, a proximity sensor, a thermocouple, and an inductive sensor.

13. The distributed computer system as claimed in claim 7, wherein the peripheral device comprises a plurality of sensors placed in multiple sensitive areas to determine one or more of (a) presence signals and (b) a position of the at least one user on a bed.

14. A computer program product for determining the quality of sleep of at least one user, the computer program product comprising at least one non-transitory computer-readable storage medium having computer-readable program code portions stored therein, said computer-readable program code portions comprising instructions for:
using a peripheral device to record a body motion signal of the at least one user, the peripheral device comprising a static sensor and a dynamic sensor;
using the peripheral device to establish a communication connection between the peripheral device and a mobile phone;
communicating the body motion signal from the peripheral device to the mobile phone; and
using the mobile phone to:
determine respiration amplitudes from the body motional signal;
detect a change in the body motion signal in a given window of time;
detect an increase or an absence of an increase in a respiration cycle amplitude in the given time window of time, wherein the respiration cycle amplitude is an average of the respiration amplitudes taken over the given window of time;
determine body posture changes of the at least one user when the change in the body motion signal and the increase in the respiration cycle amplitude are detected simultaneously;
determine body movements of the at least one user when the change in the body motion signal and the absence of the increase in the respiration cycle amplitude are detected simultaneously; and
determine the quality of sleep of the at least one user based on occurrences of the determined body posture changes and the determined body movements.

15. The computer program product as claimed in claim 14, wherein the body posture changes are further determined using a change in one or more signals determined from the body motion signal, the signals include:
a respiration cycle shape, a heartbeat cycle shape, a heartbeat cycle amplitude, and a value of presence signals.

16. The computer program product as claimed in claim 14, wherein the determination of the body posture changes of the at least one user includes:
classifying the body motion signal to feature vectors, the feature vectors associated with body postures.

17. The computer program product as claimed in claim 14, further comprising:
capturing one or more images and data of body postures of the at least one user during sleep;
storing the one or more of images and the data of the body postures of the at least one user into a data storage; and
displaying the one or more of the images and the data of the body postures a screen of the mobile phone.

18. The computer program product claimed in claim 14, wherein the dynamic sensor is one or more of a piezoelectric sensor and a piezo thin film sensor,
the static sensor is one or more of a strain gauge, a capacitive sensor, a proximity sensor, a thermocouple, and an inductive sensor, and
the peripheral device further comprises a plurality sensors placed on multiple sensitive areas to determine one or more of (a) presence signals and (b) a position of the at least one user on a bed.

* * * * *